(12) United States Patent
Cohen et al.

(10) Patent No.: US 7,378,092 B2
(45) Date of Patent: May 27, 2008

(54) IMMUNOGENIC COMPOSITIONS FOR INDUCTION OF ANTI-TUMOR IMMUNITY

(75) Inventors: Irun R. Cohen, Rehovot (IL); Varda Rotter, Rishon LeZion (IL); Roland Wolkowicz, Redwood City, CA (US); Pedro Ruiz, Stanford, CA (US); Neta Erez-Alon, Tel Aviv (IL); Johannes Herkel, Wuerzberg (DE)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 11/129,359

(22) Filed: May 16, 2005

(65) Prior Publication Data
US 2005/0208065 A1    Sep. 22, 2005

Related U.S. Application Data

(62) Division of application No. 10/032,482, filed on Jan. 2, 2002, now Pat. No. 7,118,744, which is a division of application No. 09/445,602, filed as application No. PCT/IL98/00266 on Jun. 9, 1998, now abandoned.

(30) Foreign Application Priority Data
Jun. 9, 1997    (IL) .................................. 121041

(51) Int. Cl.
*A61K 39/395* (2006.01)
*A61K 39/00* (2006.01)

(52) U.S. Cl. .............................. 424/130.1; 424/133.1; 424/138.1; 424/141.1; 424/154.1

(58) Field of Classification Search .............. 424/130.1
See application file for complete search history.

(56) References Cited

U.S. PATENT DOCUMENTS 5,874,209 A    2/1999    Karin et al. .................... 435/4

FOREIGN PATENT DOCUMENTS

| EP | 0 438 312 | 7/1991 |
|---|---|---|
| WO | WO 92/13970 | 8/1992 |
| WO | WO 93/18792 | 9/1993 |
| WO | WO 96/01126 | 1/1996 |
| WO | WO 97/04092 | 2/1997 |
| WO | WO 98/18825 | 5/1998 |

OTHER PUBLICATIONS

Gura (Science, v278, 1997, pp. 1041-1042).*
Bellone et al. . (Immunology Today, v20 (10), 1999, pp. 457-462).*
Gaiger et al. (Blood, vol. 96, No. 4, Aug. 2000, pp. 1480-1489).*
Erez-Alon et al (Cancer Research, 1998, 58:5447-5452).*
Jannot et al (BBRC, Jan. 1997, 230:242-246).*
Erez-Alon et al, Cancer Research, 1998 58:5447-5452.*

Cohen, I.R., "Natural Id-Anti-Id Networks and the Immunological Homunculus," in *Theories of Immune Networks* (Allan et al., eds.), Springer-Verlag; Heidelberg, pp. 6-12 (1989).
Cohen, I.R., "The cognitive paradigm and the immunological homunculus," *Immunol Today*, vol. 13, No. 12, pp. 490-494 (1992).
Cruse, J.M. et al., *Illustrated Dictionary of Immunology*, CRC Press, p. 148 (1994).
el-Deiry, W.S. et al., "Definition of a consensus binding site for p53," *Nature Genet*, vol. 1, No. 4, pp. 45-49 (1992).
Erez-Alon, N. et al., "Immunity to p53 induced by an idiotypic network of anti-p53 antibodies: generation of sequence-specific anti-DNA antibodies and protection from tumor metastases," *Cancer Res*, vol. 58, pp. 5447-5452 (1998).
Foord, O.S. et al., "A DNA binding domain is contained in the C-terminus of wild type p53 protein," *Nucleic Acids Res*, vol. 19, pp. 5191-5198 (1991).
Gannon, J.V. et al., "Activating mutations in p53 produce a common conformational effect. A monoclonal antibody specific for the mutant form," *Embo J*, vol. 9, No. 5, pp. 1595-1602 (1990).
Harlow, E. et al., "Monoclonal antibodies specific for simian virus 40 tumor antigens," *J Virol*, vol. 39, pp. 861-869 (1981).
Hollstein, M. et al., "p53 mutations In human cancers," *Science*, vol. 253, pp. 49-53 (1991).
Houbiers, J.G. et al., "In vitro induction of human cytotoxic T lymphocyte responses against peptides of mutant and wild-type p53," *Eur J Immunol*, vol. 23, pp. 2072-2077 (1993).
Jannot, C.B. et al., "Characterization of scFv-421, a Single-Chain Antibody Targeted to p53", *Biochem Biophys Res Comm*, vol. 230, No. 2, pp. 242-246 (1997).
Lee, S. et al., "p53 and its 14Kda C-terminal domain recognize primary DNA damage in the form of insertion/deletion," *Cell*, vol. 81, pp. 1013-1020 (1995).
Lubin, R. et al., "Analysis of p53 30 antibodies in patients with various cancers define B-cell epitopes of human p53) distribution on primary structure and exposure on protein surface", *Cancer Res*, vol. 53, pp. 5872-5876 (1993).

(Continued)

*Primary Examiner*—Misook Yu
*Assistant Examiner*—Sean E Aeder
(74) *Attorney, Agent, or Firm*—Winston & Strawn LLP

(57) ABSTRACT

The invention relates to methods of inducing an anti-tumor immunity and/or inducing an immune responses to p53 in mammals. The methods comprise administering to a mammal an effective amount of at least one immunogen selected from the group consisting of:

(i) a peptide based on a CDR of the heavy or light chain of an anti-p53 mAb, which peptide is capable of eliciting antibodies to p53; and (ii) a DNA molecule coding for the variable (V) region of an anti-p53 mAb in a suitable gene delivery vehicle. Preferably the immunogen is administered in the form of a pharmaceutical composition.

Preferably the peptide is 7 to 30 amino acid residues in length and contains a sequence of the CDR2 or CDR3 of the heavy chain, or of the CDR3 of the light chain of an anti-p53 mAb.

24 Claims, 5 Drawing Sheets

OTHER PUBLICATIONS

Nicholson, A.G. et al., "Anti-tumor immune responses following monoclonal antibody therapy of ovarian cancer," *Proc Ann Meet Am Assoc Cancer Res*, vol. 38 (XP002081861) (1997).

Nisonoff, A. et al., "Idiotypes: concepts and applications," *J Immunol*, vol. 147, pp. 2429-2438 (1991).

Paul, W.E., *Fundamental Immunology*, Raven Press, NY, Chapter 8, p. 242 (1993).

Ruiz, P.J. et al., "Idiotypic immunization induces immunity to mutated p53 and tumor rejection," *Nature Med*, vol. 4, No. 6, pp. 710-712 (1998).

Schlichtholz, B. et al., "The immune response to p53 in breast cancer patients is directed against immunodominant epitopes unrelated to the mutational hot spot," *Cancer Res*, vol. 52, pp. 6380-6384 (1992).

Soussi T., "The humoral response to the tumor suppressor gene product p53 in human cancer. Implications for diagnosis and therapy," *Immunol Today*, vol. 17. p. 354-356 (1996).

Stevenson, F.K. et al., "Idiotypic DNA vaccines against B-cell lymphoma," *Immunol Rev.*, vol. 145, pp. 211-228 (1995).

Tilkin A-F. et al., "Primary proliferative T cell response to wild-type p53 protein in patients with breast cancer," *Eur J Immunol*, vol. 25, pp. 1765-1769 (1995).

Wolkowicz, R. et al., "The DNA binding activity of wild type p53 is modulated by blocking its various antigenic epitopes," *Oncogene*, vol. 10, pp. 1167-1174 (1995).

Yanuck, M. et al., "A mutant p53 tumor suppressor protein is a target for peptide-induced CD8+ cytotoxic T-cells," *Cancer Res*, vol. 53, pp. 3257-3261 (1993).

Zusman, I. et al., "Tumor-Suppressor effects of anti-p53 IgG on chemical induced colon cancer in rats," *Cancer J*, vol. 110, No. 2, pp. 116-120 (1997).

* cited by examiner

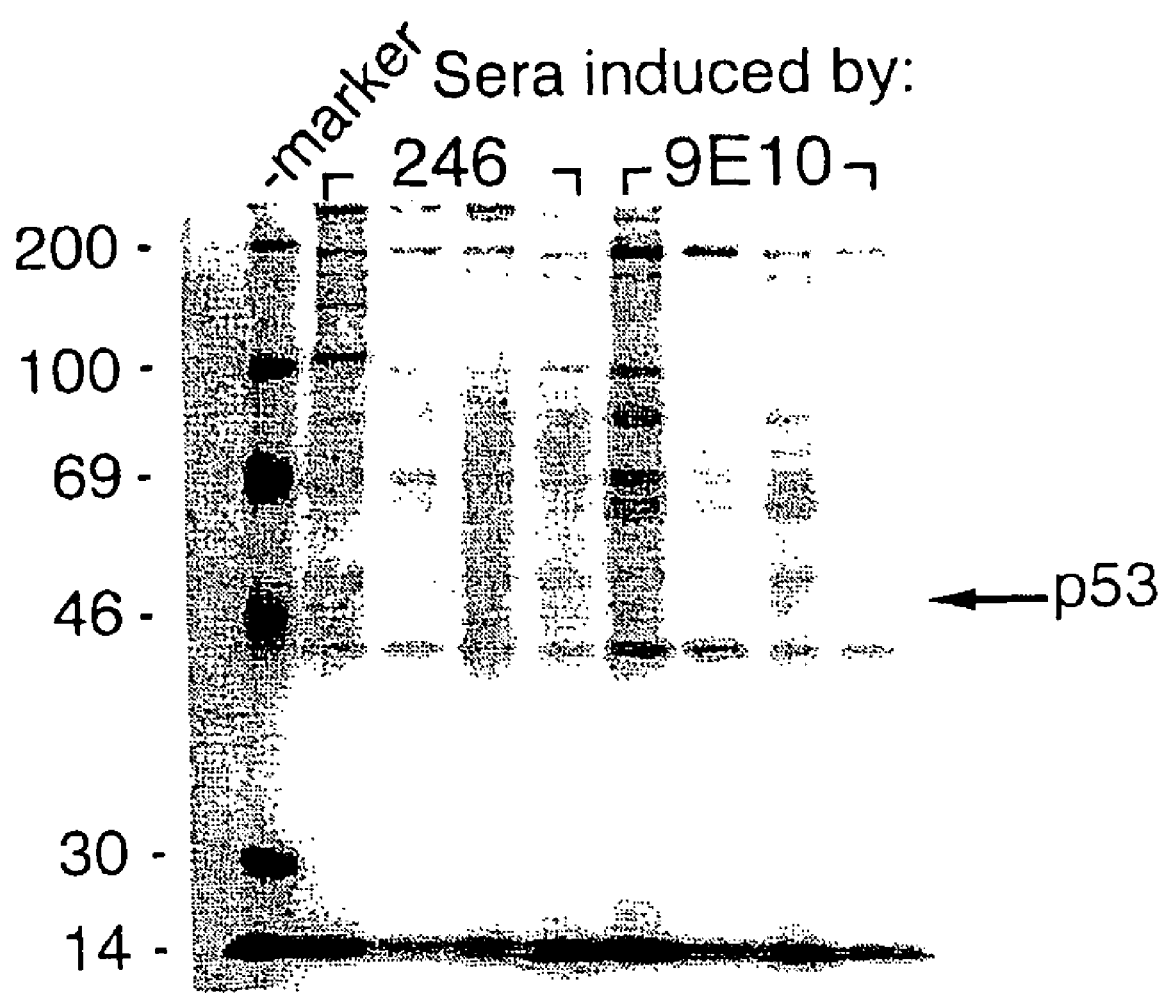

Figure 3

240 VH:
ATGEAGASVKLSCKASGYTFT<u>SSWIN</u>WVKQRPGQGLEWIG<u>EIDPSDSYTN
YNQNFKD</u>KATLTVDKSSSTAYMQLSSLTSEDSAVYYCAR<u>LLRYFAMDY</u>WG
QGTT

246 VH:
SWVKPGASVKIPCKASGYTFT<u>DYNMD</u>WVKQSHGKSLEWIG<u>DINPNNGYTI
YNQKVKG</u>KATLTVDKSSNTAYMELRSLTSEDTAVYYCVR<u>GGGLKGYPFVY</u>
WGQGTT

248 VH:
LQESGPELVKPGASVKISCKASGYTFT<u>DYYMN</u>WVKQSHGKSLEWIG<u>DIYPN
NGFTTYNQKFKG</u>KATLTVDKSSSTAYNELRNLTSEDSAVYYCAR<u>SGSRFD
YW</u>GQGTTVHR

421 VH:
LQESGAELVRSGASVKLSCTASGFNIK<u>DYYMH</u>WVKQRPEQGLEWIG<u>WIDP
ENGDTEYAPKFQG</u>KATMTADTSSNTAYLQLSSLASEDTAVYYCNF<u>YGDAL
DY</u>WGQGTTVTVS

240 VL:
FLSCISGAEGHHLIQGQQKC<u>QYIWLYYMH</u>WNQQKPGQPPRLLIY<u>LVSNLE</u>
SGVPARFSGSGSGTDFTLNIHPVEEEDAATYYC<u>QHIRELTR</u>SEGGPSWRSI
RI

246 VL:
KVTITC<u>SASSSVNFMH</u>WFQQKPGTSPKLWIY<u>STSNLAS</u>GVPARFIGSGSGT
S?SLTISRMEAEHAATYYC<u>QQRSSFPFT</u>YGSGTK?EIQ?DP

248 VL:
MDIQLTQSPATLSVTPGDSVSLSC<u>RASQSISNNLH</u>WYQQKSHESPRLLIKF
<u>ASQSIS</u>GIPSRFSGSGSGTDFTLSINSVETEDFGVYFC<u>QQSNSWPVH</u>ARG
GGTKLENL

421 VL:
PQDIQLTQSPLTLSVTIGQPASISC<u>KSSQSLLDSDGKTYLN</u>WLLQRPGQSP
KRLIY<u>LVSKLDS</u>GVPDRFTGSGSGTDFTLKINRVEAEDLGVYYC<u>WQGTHSP
LT</u>FGAGTKLK

US 7,378,092 B2

IMMUNOGENIC COMPOSITIONS FOR INDUCTION OF ANTI-TUMOR IMMUNITY

CROSS-REFERENCE TO RELATED APPLICATIONS

The present application is a divisional of U.S. application Ser. No. 10/032,482, filed on Jan. 2, 2002 now U.S. Pat. No. 7,118,744, which is a divisional of U.S. application Ser. No. 09/445,602, filed on Mar. 23, 2000, now abandoned, which is the national stage under 35 U.S.C. § 371 of International Application No. PCT/IL98/00266, filed on Jun. 9, 1998, the entire contents of which are incorporated herein by reference.

FIELD OF THE INVENTION

The present invention relates to the use of an immunogenic composition for the induction of anti-tumor immunity in mammals, said composition comprising a pharmaceutically acceptable carrier and an immunogen selected from the group consisting of: (i) a monoclonal antibody (mAb) to the tumor-associated antigen (TAA) p53, (ii) a fragment of an anti-p53 mAb, (iii) a peptide based on a complementarity-determining region (CDR) of an anti-p53 mAb, which peptide is capable of eliciting antibodies to p53, and (iv) a nucleic acid sequence coding for the variable region of an anti-p53 mAb, and to a method for induction of anti-tumor immunity in a subject comprising administration of said immunogen.

ABBREVIATIONS

The following abbreviations will be used herein in the specification and claims: anti-id—anti-idiotype; mAb—monoclonal antibody; TAA—tumor-associated antigen; CDR—complementarity-determining region of the heavy or light chain of a m-Ab.

BACKGROUND OF THE INVENTION

The rejection of transplanted cells and tissues of allogeneic origin proves that the immune system is capable of destroying its targets. It has long been a goal of immunologists to direct the destructive capability of the immune system against a person's tumor cells and thereby effect the rejection of the tumor and the cure of the patient. Immunotherapy would be especially useful to rid a person of residual tumor cells that have spread beyond the site of the primary tumor mass. The primary tumor can usually be resected surgically or irradiated by local radiotherapy. The patient too often succumbs later, however, to metastatic tumor cells that have spread to other parts of the body. Immunotherapy would be an ideal way to destroy nests of metastatic tumor cells before they grow into large fife-threatening tumors. Lymphocytes patrol the tissues and lymphocytes sensitized to the tumor cells could kill the metastatic tumor cells remaining after resection of the primary tumor mass.

The problem for immunotherapy, however, is to activate the immune system against antigens that can mark the tumor cells for destruction. It had been hoped that tumors might bear "foreign transplantation" antigens produced by viruses or created by immunologically significant mutations of genes in the tumor cell. It now turns out that such tumor specific transplantation antigens (TSTA) are rare.

Tumor cells are characterized immunologically for the most part by TAA, which are molecules that are expressed in normal cells too. These TAA may appear normally during the early development of healthy cells, or they may be expressed normally at lower concentrations than in tumor cells. TAA may also feature minor mutations that do not appear "foreign" to the immune system and thus do not stimulate strong immune responses. TAA, for the most part, are self-antigens and, as such, they are not very immunogenic. The immune system is normally tolerant to the body's own antigens. Therefore, the induction of effective immunity against TAA is tantamount to inducing an autoimmune reaction. Immunotherapy of tumors requires the activation of the equivalent of an autoimmune reaction against the tumor cells. Moreover, it is most desirable to have the autoimmune reaction limited to the tumor itself, so the autoimmune reaction terminates once the tumor cells are destroyed. Nevertheless, autoimmunity can be compatible with life, while metastatic cancer can kill. Therefore, residued autoimmunity is a tolerable price to pay for successful tumor immunotherapy.

Examples of known TAA include p53 protein, neu differentiation factor (NDF), epidermal growth factor (EGF), carcinoembryonic antigen (CEA), and tyrosinase enzyme.

The p53 protein is the product of a tumor suppressor gene that functions to arrest the growth of mutated or aberrant cells. The p53 protein is a transcription factor that binds specifically to a consensus site present in the regulatory sequences of p53-dependent genes (el-Deiry et al., 1992; Zambetti and Levine, 1993). Mutation of the p53 gene in the domain encoding binding to the specific DNA regulatory site causes a loss of tumor suppression (Zambetti and Levine, 1993). Therefore it is not surprising that a significant proportion of natural human tumors bear mutated p53 (Hollstein et al., 1991). For reasons that are-not entirely clear, tumor cells also appear to accumulate wild-type p53 and not only mutated p53 in their cytoplasm (Moll et al., 1995). Thus the wild-type p53 molecule, and not only the mutated p53 molecule, can serve as a target for a potentially therapeutic anti-tumor immune response.

Inactivation of the p53 tumor suppressor protein by mutation of the gene or by viral insertion, gene rearrangement, or other causes is a common event in human cancers. Point mutation or deletion of the p53 gene is the most common genetic aberration in human neoplasms. Approximately 70% of colon cancers, 30 to 50% of breast cancers, 50% of lung cancers, and almost 100% of small-cell carcinomas of the lung harbor p53 mutations (Hollstein et al., 1991). The development of a tumor is often associated with accumulation in the cancer cells of the p53 protein, wild-type or mutant. Furthermore, mutated p53 proteins are tumor-specific antigens that can be recognized as targets by the immune system (Melief and Kast, 1991; Yanuck et al., 1993). Cancer patients can manifest immune responses directed to wild-type and mutant p53 proteins. The p53 protein, mutant and wild-type, can accumulate in the cytoplasm of cancer cells, and cancer patients have indeed been found to produce antibody (Lubin et al., 1993; Schlichtholz et al., 1992) and T cell responses to p53 (Houbiers et al., 1993; Tilkin et al., 1995). Normal cells express p53 to a much lower degree and, unlike tumor cells, normal cells show no accumulation of p53 in the cytoplasm. Thus, tumor cells and normal cells differ in both the amount and compartment of p53 expression. For these reasons, the wild-type p53 molecule, and not only the mutated p53 molecule, can serve as a target for a potentially therapeutic anti-tumor immune response.

To identify T-cell epitopes in p53, Houbiers et al., 1993, synthesized peptides of wild-type p53 and peptides with the point mutations of p53 detected in colorectal and ovarian cancers. Some of the p53 peptides were shown to bind in vitro to HLA-A2.1 molecules and to induce specifically cytotoxic T lymphocytes (CTL) clones. Characterization of anti-p53 immunity and its implications for tumor therapy have been studied using peptides derived from wild-type or mutated p53 sequences to elicit CTL responses in experimental animals (Noguchi et al., 1994; Noguchi et al., 1995; Yanuck et al., 1993). Mouse fibroblasts transfected with a mutated human p53 gene were specifically killed by $CD8^+$ CTL from the spleens of mice that had been pulsed with a 21-amino acid peptide encompassing a p53 point mutation from a human lung carcinoma (Yanuck et al., 1993). A nonapeptide containing a codon 234 mutation (234CM) induced $CD8^+$ CTL that lysed a 234CM-pulsed PIHTR mastocytoma cell line (Noguchi et al., 1994). Mice immunized with peptide 234CM were resistant to challenge with Meth A sarcoma cells (Noguchi et al., 1994), and vaccines containing peptide 234CM in the QS-21 adjuvant caused regression of established Meth A tumors in mice treated with IL-12 (Noguchi et al., 1995).

Thus, both mutated p53 and wild-type p53 are tumor-associated antigens and attempts have been made to use these molecules as immunogens for tumor immunotherapy (Houbiers et al., 1993; Noguchi et al., 1994; Noguchi et al., 1995; Yanuck et al., 1993; published PCT Application WO 94/02167). However, p53 is not very immunogenic, probably because it is a self-protein and therefore immunologically tolerated.

An antibody binds to an antigen at its variable region (antigen-binding site). Therefore, the variable regions of antibodies have three-dimensional structures that are complementary to the structures of the antigenic determinants the antibodies recognize.

The binding site of the antibody complementary to the structure of the antigen is created by hypervariable regions of the light and heavy chains of the Fab portion of the antibody. These binding site structures are formed by the collective aggregate of the CDR of the light and heavy chains of the immunoglobulin molecule (Alzari et al., 1988). However, an antibody itself, when recognized by another antibody, can be considered to be an antigen. In the case where structures of the variable regions of the antibody are recognized, these structures are called idiotypes Gd), and the antibodies that recognize the idiotypes of the antibody are called anti-idiotypic (anti-id) antibodies. The structure corresponding to the antigenic determinant of the antibody is called an idiotope (Jerne, 1974).

It has been reported that immunization with mAbs can induce immune responses that extend beyond the specificity of the antibody (Takemori et al., 1982), probably by anti-idiotypic connectivity (Jerne, 1974; Cohen, 1989, 1992) based on idiotypic determinants in the variable (V) region of the immunizing mAb Bruggemann et al., 1980). According to idiotypic antibody network terminology, Ab1 is the first antibody, the antibody binding to the antigen, and Ab2 is the anti-idiotypic antibody to Ab1. The variable region of Ab2 may mimic the conformation of the antigen because both the antigen and Ab2 can be bound by Ab1. Ab3 is the anti-idiotypic antibody to Ab2. Because of the chain of structural complementarity, Ab1 and Ab3 can have similar specificity for the original antigen.

Antibodies have been used in the past in tumor immunotherapy in two ways: Ab1 antibodies as tumor-specific antigens on B lymphoma cells, and Ab2 antibodies as anti-idiotypic mimics of tumor antigens. Ab1 idiotypic determinants expressed by immuno globulins on the surface of neoplastic B cells have been used in experimental models as tumor-associated targets to induce protective immunity (Ab2) against B cell lymphomas which, unlike solid tumors, are particularly sensitive to antibodies (reviewed by Yefenof et al., 1993). However, Ab1 idiotypic determinants are unique to each B-cell tumor, and the practical requirements of preparing an individual protein vaccine for each patient has made the application to the clinic difficult and expensive (Stevenson et al., 1995).

Ab2 antibodies mimicking TAAs of various kinds have been used to induce antibodies (Ab3) to tumor antigens (reviewed by Wettendorf et al., 1990). However, Ab2 immunization has been usually less successful than has immunization with the TAAs themselves, (Wettendorf et al., 1990).

With regard to the possible anti-cancer effects of anti-p53) antibodies, cancer patients have been found to produce antibodies to the amino terminus of the p53 molecule, but these antibodies appear to mark the development of cancer rather than to protect against the disease (Soussi, 1996). Investigation of the effects of immunity to the central and carboxy domains of p53 might therefore be of some importance.

Published International PCT Application No. WO 94/12202 describes the activation of a mutant p53 that occurs at elevated levels in tumors and does not substantially suppress tumor growth, for specific DNA binding, wherein the mutant p53 is activated with a ligand capable of binding to, and activating the mutant p53), wherein the ligand may be the anti-p53 mAb 421 which binds to the carboxy terminal region of p53, or the bacterial heat shock protein DnaK, or a ligand which binds effectively to the same site on the mutant p53.

SUMMARY OF THE INVENTION

It is an object of the present invention to provide a novel way of inducing effective anti-tumor immunity without apparent harm to the patient.

It has now been found in accordance with the present invention that immunization of BALB/c or C57BL/6 mice with anti-p53 mAbs (Ab1) directed to different domains of the p53 molecule induces spontaneously antibodies to p53 (Ab3), and that anti-DNA antibodies (Ab2) are generated if Ab1 is directed to a DNA-binding domain of p53.

The present invention thus relates to the use of an immunogen selected from the group consisting of:
 (i) an anti-p53 mAb;
 (ii) a fragment of an anti-p53 mAb;
 (iii) a peptide based on a CDR of the heavy or light chain of an anti-p53 mAb, which peptide is capable of eliciting antibodies to p53; and
 (iv) a DNA molecule coding for the variable (V) region of an anti-p53 mAb in a suitable gene delivery vehicle, for the preparation of a pharmaceutical composition useful for induction of anti-tumor immunity in mammals, for activating an enhanced immune response to a p53 molecule in mammals, and/or for induction of immune responses to mutated and wild-type forms of p53 in mammals.

In another aspect, the present invention relates to methods for induction of anti-tumor immunity in a mammal, for activating an enhanced immune response to p53 in a mammal, and/or for induction of immune responses to mutated and wild-type forms of p53 in a mammal, which comprises administering to said mammal an effective amount of an immunogen selected from the group consisting of:

(i) an anti-p53 mAb;
(ii) a fragment of an anti-p53 mAb;
(iii) a peptide based on a CDR of the heavy or light chain of an anti-p53 mAb, which peptide is capable of eliciting antibodies to p53; and
(iv) a DNA molecule coding for the variable (V) region of an anti-p53 mAb in a suitable gene delivery vehicle.

The anti-p53 mAb used according to the invention may be directed against different domains of wild type p53 or a mutant p53, and may be a murine, human or humanized anti-wild type or anti-mutant p53 mAb.

The anti-p53 mAb fragments that can be used according to the invention include antigen-binding fragments (Fab), F(ab')2 or any other type of antibody molecule, including single chain Fv fragments of antibodies, as long as such antibody fragments are able to bind p53 as well as peptides based on a CDR of the heavy or light chain of an anti-p53 mAb, which peptides are capable of eliciting antibodies to the p53 without necessarily binding p53.

In still a further aspect, the present invention relates to a method for the generation of sequence-specific anti-DNA antibodies which comprises immunizing a mammal with a mAb directed to a domain containing a DNA-binding site of a DNA-binding protein, e.g. p53, and recovering the thus elicited sequence-specific anti-DNA antibodies.

BRIEF DESCRIPTION OF THE DRAWINGS

FIGS. 2A-2B show immunoprecipitation of labeled p53 produced by reaction of an extract of Meth A tumor cells, metabolically labeled with $^{35}$S-methionine, with anti-p53 mAbs 421, 246 and 240 (FIG. 2A) or with antisera induced by immunization with mAbs 421, 240 (FIG. 2A), or mAb 246 and control 9E 10 (FIG. 2B).

FIG. 3 shows the sequences (SEQ ID NO:1 to SEQ ID NO:8) of the heavy (VH) and light (VL) chains of the anti-p53 mAbs 240, 246, 248 and 421, in which the CDR sequences are underlined.

DETAILED DESCRIPTION OF THE INVENTION

Figure 1:
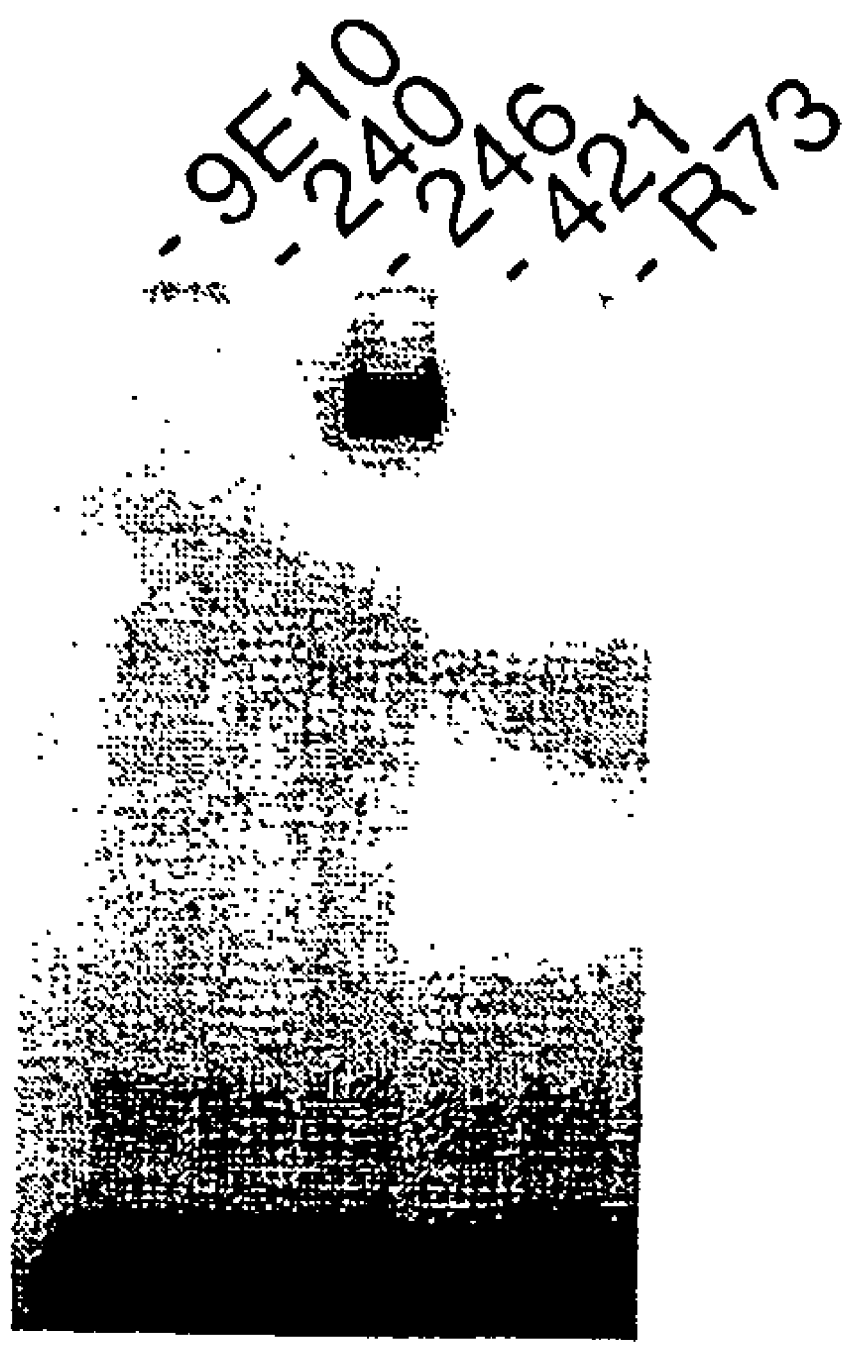
FIG. 1 shows the retardation in gel of the p53-specific oligonucleotide sequence by anti-DNA antibodies developed in mice immunized with anti-p53 mAb 246, but not with mAb 240, mAb 421, mAb 9E 10 and mAb R73.

The present invention relates, in one aspect, to the use of an Ab1 anti-p53 mAb to generate an Ab3 anti-p53 response. Presumably, the chain reaction from Ab1 to Ab3 implies the generation of Ab2 antibodies as intermediates.

To activate an enhanced immune response to p53 according to the invention, an anti-idiotypic; network (reviewed by Nisonoff, 1991) inducible by immunization with antibodies as immunogens rather than with antigens, was exploited.

The p53 molecule has two attributes of immunological interest: (a) because p53 binds DNA, immunity to p53 may lead to anti-DNA antibodies by an anti-id network: antibodies to a DNA-binding site of p53 can mimic DNA and, therefore, such anti-p53 antibodies might induce anti-DNA antibodies as anti-ids; and (b) because p53 accumulates in transformed cells, immunity to p53 may have an anti-tumor effect.

The generation of antibodies to DNA has been difficult because the DNA molecule is poorly immunogenic. In particular, it would be desirable to obtain antibodies to specific DNA sequences as such antibodies can be used to detect the presence of such sequences for purposes of diagnosing whether an individual has a specific gene or promoter sequence. A specific antibody would have an advantage over currently used PCR (polymerase chain reaction) techniques, because antibody binding, unlike the PCR, is easily quantifiable and needs no primers or enzymatic replication. In particular, sequence-specific anti-DNA antibodies can be used in diagnostics, for example, in detecting critical sequences in the breeding of animals and plants, in the identification of bacteria and other parasites, in determination of paternity and maternity, in forensic medicine. Specific anti-DNA antibodies also can be useful in the isolation of specific genes for DNA vaccination, gene cloning, and gene sequencing. Antibodies to specific sequences of DNA might also have a use in the activation or inhibition of particular genes for therapeutic purposes in plants, animals or humans. It has been shown that antibodies penetrate into living cells (Alarcon-Segovia et al., 1996; Madaio et al., 1996; Yanase et al., 1994; Ma et al., 1991) and anti-DNA antibodies might be able to exert effects within living cells. But DNA in general, and certainly specific sequences of mammalian DNA, are not immunogenic.

According to the present invention, the p53 molecule was used as model of a DNA-binding protein in order to learn whether sequence-specific anti-DNA antibodies might be generated by an anti-id network centered around immunity to a DNA-binding protein. The p53 molecule might serve as a model of a well-characterized DNA-binding protein that recognizes a highly specific p53 regulatory site (el-Deiry et al., 1992). This domain makes it possible for the p53 molecule to bind to the p53-specific DNA regulatory site, leading to growth arrest of the aberrant cell. Antibodies to the specific DNA-binding, site of p53 can be used to determine whether specific anti-DNA antibodies (as Ab2) can be generated, by way of an anti-id network, using antibodies to the specific DNA-binding domain of p53 (as Ab1). Because of the structural similarity between DNA and RNA, it is obvious that the specific anti-DNA antibodies could also recognize specific RNA.

Induction of an immune response to specific DNA (Ab2) and to mutated and wild-type forms of p53 (Ab3) is provided according to the invention by immunization with mabs (Ab1) specific for particular domains of wild-type or mutated p53 proteins. The induction of anti-p53 antibodies (Ab3) is hereon shown to be associated with the development of resistance to challenge with a murine fibrosarcoma tumor Meth A and with inhibition of lung metastases produced by the spontaneously metastazing 3LL tumor. Since over-expression and/or accumulation of p53 antigen is common to many tumors, immunization with antibodies directed to the p53 protein, by eliciting an idiotypic network response, may be useful in the development of a general therapy for different cancers, particularly since effector T cells are activated in such networks.

The induction of specific anti-DNA antibodies by immunization with a mAb to the domain of p53 that binds specific DNA indicates that anti-DNA antibodies can indeed arise by an anti-id network. Thus, the anti-id network appears to preserve structural similarity with particular p53 domains.

Thus, in particular embodiments of the present invention, immunization either with an anti-mutant p53 mAb such as mAb 240 that is specific for a mutated p53) conformation (Gannon et al., 1990), or with an anti-wild type p53 mAb such as mAb 246 that is specific for the native conformation of p53, at the edge of the DNA-binding site of native p53 (Yewdell et al., 1986), or with a mAb against both the wild-type and mutant p53, such as mAb 421 that is specific for the carboxy terminal domain of p53 conserved in both wild-type and mutant p53 (Arai et al., 1986), induced anti-p53 antibody titers both in BALB/c and in C57BL/6mice, apparently by way of an anti-idiotypic network. This anti-p53 immunity was associated with the acquisition of the ability to reject both primary tumors and metastatic tumors.

However, the development of specific anti-DNA antibodies (Ab2) varied with the domain of p53 recognized by the Ab1 used to activate the network. Both the mAb 240 specific for mutated p53, and the mAb 421 specific for the carboxy terminus, did not induce sequence-specific anti-DNA antibodies. However, the mAb 246 induced antibodies to the p53-specific DNA sequence. Thus, sequence-specific anti-DNA antibodies can be produced by immunization with anti-p53 mAbs specific to the central DNA-binding domain of p53, such as mAb 246; and generation of anti-DNA antibodies can be avoided by the use of an anti-P53 antibody, such as mAb 240, that does not bind a domain of p53 that binds to DNA.

The present invention encompasses the use of any anti-p53 mAb, or a fragment thereof. Since different mutations of p53 may generate a common mutant conformation (Gannon et al. 1990), it may not be necessary to tailor a mAb to each mutation of p53. Thus, according to the present invention, anti-p53 mAbs to either native or mutant p53 can serve as immunotherapeutic agents of wide applicability in the treatment of cancer. The therapeutic anti-p53 mAbs can be of various kinds, including murine, human, or "humanized" mouse antibodies, all of them isolated or prepared in different ways by standard procedures.

Anti-p53 mAb fragments according to the invention include antigen-binding fragments (Fab), F(ab')2 or any other type of antibody molecule, including single chain Fv fragments of antibodies, as long as such antibody fragments are able to bind to p53.

The use of genetically engineered humanized mAb or of mAb fragments may be preferred according to the invention because they minimize the amount of foreign protein to be injected and avoid an immune response that may be generated against a murine mAb.

The structural correlates of idiotopes that define the unique binding specificities of antibodies include the CDR hypervariable segments of the immunoglobulin heavy and light chains (Alzari et al., 1989). Thus, according to the present invention, synthetic peptides containing the sequence of a CDR of the heavy or light chain of an anti-p53 mAb, and not only the intact mAb molecule, induce anti-p53 immunity by the anti-idiotypic network.

The invention thus further relates to synthetic peptides based on a CDR of the heavy or light chain of an anti-p53, mAb, and salts and chemical derivatives thereof. Examples of such peptides are peptides containing one or more of the sequences of the CDR2 and CDR3 of the heavy chain and of the CDR3 of the Light chain of the mAbs against p53, which sequences are underlined in FIG. 3 as follows:

(i) Peptides, herein designated Ia-Ib, based on the CDR2 and CDR3, respectively, of the heavy chain (240VH) and peptide Ic based on the CDR3 of the light chain (240VL), of the anti-p53 mAb 240, of the sequences:

(Ia)    Glu-Ile-Asp-Pro-Ser-Asp-Ser-Tyr-Thr-  (SEQ ID NO:9)
        Asn-Tyr-Asn-Gln-Asn-Phe-Lys-Asp (Ib)    Leu-Leu-Arg-Tyr-Phe-Ala-Met-Asp-Tyr  (SEQ ID NO:10)

(Ic)    Gln-His-Ile-Arg-Glu-Leu-Thr-Arg  (SEQ ID NO:11)

(ii) Peptides, herein designated IIa-IIb, based on the CDR2 and CDR3, respectively, of the heavy chain (246VH), and peptide IIc based on the CDR3 of the light chain (246VL), of the anti-p53 mAb 246, of the sequences:

(IIa)   Asp-Ile-Asn-Pro-Asn-Asn-Gly-Tyr-Thr-  (SEQ ID NO:12)
        Ile-Tyr-Asn-Gln-Lys-Val-Lys-Gly (IIb)   Gly-Gly-Gly-Leu-Lys-Gly-Tyr-Pro-Phe  (SEQ ID NO:13)
        Val-Tyr (IIc)   Gln-Gln-Arg-Ser-Ser-Phe-Pro-Phe-Thr  (SEQ ID NO:14)

(iii) Peptides, herein designated IIIa-IIIb, based on the CDR2 and CDR3, respectively, of the heavy chain (248VH), and peptide IIIc based on the CDR3 of the light chain (248VL), of the anti-p53 mAb 248, of the sequences:

(IIa)   Asp-Ile-Tyr-Pro-Asn-Asn-Gly-Phe-Thr  (SEQ ID NO:15)
        Thr-Tyr-Asn-Gln-LysPhe-Lys-Gly (IIb)   Ser-Gly-Ser-Arg-Phe-Asp-Tyr  (SEQ ID NO:16)

(IIc)   Gln-Gln-Ser-Asn-Ser-Trp-Pro-Val-His  (SEQ ID NO:17)
        Ala (iv) Peptides, herein designated IVa-IVb, based on the CDR2 and CDR3, respectively, of the heavy chain (421VH), and peptide IVc based on the CDR3 of the light chain (421VL), of the anti-p53 mAb 421, of the sequences:

(IVa)   Trp-Ile-Asp-Pro-Glu-Asn-Gly-Asp-Thr-  (SEQ ID NO:18)
        Glu-Tyr-Ala-Pro-Lys-Phe-Gln-Gly (IVb)   Tyr-Gly-Asp-Ala-Leu-Asp-Tyr  (SEQ ID NO:19)

(IVc)   Trp-Gln-Gly-Thr-His-Ser-Pro-Leu-Thr  (SEQ ID NO:20)

A "chemical derivative" of a peptide of the present invention, as defined herein, contains additional chemical moieties not normally a part of the peptide. Covalent modifications of the peptides are included within the scope of the invention. Such modifications may be introduced into the molecule by reacting targeted amino acid residues of the peptide with an organic derivatizing agent that is capable of reacting with selected side chains or terminal residues. Such derivatives include, but are not limited to, esters, N-acyl derivatives, and the like. Many such chemical derivatives and methods of making them are well known in the art.

Also included in the scope of the invention are salts, both organic and inorganic, of the CDR-based peptides.

The peptides according to the invention have preferably 9-30 amino acid residues, examples of which are the 17- to 21-mer peptides V, VI, VII, VIII and IX, which are based on the CDR sequences mentioned above as follows: peptide V includes the sequence Ic of the CDR3 of the light chain of mAb 240, peptide VI includes the sequence IVc of the CDR3 of the light chain of mAb 421, peptide VII includes the sequence IIa of the CDR2 of the heavy chain of mAb 246, peptide VIII includes the sequence IIIb of the CDR3 of the heavy chain of mAb 248, and peptide IX includes the sequence IIIc of the CDR3 of the light chain of mAb 248.

| | SEQ ID NO:21 |
|---|---|
| Peptide V: | Tyr-Tyr-Cys-Gln-His-Ile-Arg-Glu-Leu-Thr-Arg-Ser-Glu-Gly-Gly-Pro-Ser |

| | SEQ ID NO:22 |
|---|---|
| Peptide VI: | Gly-Val-Tyr-Tyr-Cys-Trp-Gln-Gly-Thr-His-Ser-Pro-Leu-Thr-Phe-Gly-Ala-Gly-Thr-Lys |

| | SEQ ID NO:23 |
|---|---|
| Peptide VII: | Gly-Asp-Ile-Asn-Pro-Asn-Asn-Gly-Tyr-Thr-Ile-Tyr-Asn-Gln-Lys-Val-Lys-Gly-Lys-Ala |

| | SEQ ID NO:24 |
|---|---|
| Peptide VIII: | Ala-Val-Tyr-Tyr-Cys-Ala-Arg-Ser-Gly-Ser-Arg-Phe-Asp-Tyr-Trp-Gly-Glu-Gly-Thr-Thr |

| | SEQ ID NO:25 |
|---|---|
| Peptide IX: | Val-Tyr-Phe-Cys-Gln-Gln-Ser-Asn-Ser-Trp-Pro-Val-His-Ala-Arg-Gly-Gly-Gly-Thr-Lys |

The present invention also provides a DNA sequence coding for the variable region of a mAb to p53, in a suitable gene delivery vehicle. Any gene delivery vehicle such as viral vectors, e.g. recombinant retroviral vectors and recombinant adenovirus vectors, naked DNA nucleic acid molecules such as plasmids, liposomes, bacterial and eukaryotic cells, as well as other suitable vehicles as described in Vile and Russell, 1994, and in published PCT Application WO 96/21015, both references herein incorporated by reference, can be used according to the invention.

According to the invention, the immunogens can be used for treatment of primary, as well as metastatic, tumors of any kind, including but not being limited to brain, breast, ovarian, uterus, skin, lung, esophagus, colon, prostate, kidney and bladder cancers, leukemias and lymphomas.

A pharmaceutical composition according to the invention comprising an anti-p53 mAb, a fragment thereof or a peptide based on a CDR region of the heavy or light chain of an anti-p53 mAb, together with a pharmaceutically acceptable carrier, can be administered through various routes known in the art, such as oral, intranasal, intravenous, subcutaneous, intramuscular, intraperitoneal, transdermal or other known routes including the enteral route. In a preferred embodiment, the composition comprising the anti-p53 mAb, fragment or CDR-based peptide, is administered subcutaneously.

When the immunogen is a DNA molecule coding for the variable region of an anti-p53 mAb, it is administered in a suitable gene delivery vehicle as described (Vile and Russel, 1994; WO 96/21015).

The dosage of the immunogen to be administered will depend on the type of compound used—a mAb, a fragment or a peptide, and upon the age, sex, weight and condition of the recipient. The doses should not be so large as to cause adverse side effects such as unwanted cross-reactions, generalized immunosuppression, anaphylactic reactions and the like.

It is also encompassed by the present invention to administer to a patient effective amounts of two or more different anti-p53 mAbs, or fragments thereof. The different mAbs or fragments thereof may be administered concomitantly or sequentially at different intervals.

It is further encompassed by the present invention to administer to a patient effective amounts of two or more different peptides based on the same or different CDR regions of the same anti-p53 mAb or of different anti-p53 mabs. The different peptides may be administered concomitantly or sequentially at different intervals.

Having now generally described the invention, the same will be more readily understood through reference to the following examples.

EXAMPLES

Materials and Methods (i) Mice (a) Female mice of the BALB/c strain were obtained from Olac, Oxon, UK, and used at the age of 8-10 weeks.

(b) Female mice of the inbred strain C57BL/6 were used at the age of 6-10 weeks. The mice were bred and kept at the animal breeding facilities of the Weizmann Institute of Science, Rehovot.

(ii) Monoclonal Antibodies (MAb)

The following mouse monoclonal antibodies (all IgG1/κ) were used: mAb 240, specific for a mutated non-DNA binding conformation of the p53 molecule (Gannon et al., 1990); mAb 246, specific for the native conformation of p53 at the edge of the p53-specific DNA binding site (Cook and Milner, 1990; Yewdell et al., 1986); mAb 421, specific for the carboxy domain of p53 (Aral et al., 1986) and the anti-myconco-protein antibody mAb 9E10 (Munro and Pelham, 1986), used as a control antibody. R73 is a mouse-anti rat-T cell receptor monoclonal antibody (IgG1)(Hunig et al., 1989) and was used as a control antibody.

The antibodies were obtained by growing the hybridomas as ascites in BALB/c mice, collecting the ascitic fluids and purifying the antibodies by protein A affinity chromatography followed by dialysis in PBS.

(iii) Tumor Cells (a) The Meth A tumor is a transplantable 3-methylcholantrene-induced sarcoma of BALB/c origin (Old et al., 1962) that has three mutations in the p53 coding sequence (Arai et al., 1986). The cells were grown in DMEM containing 10% heat-inactivated fetal calf serum (FCS), and passaged through BALB/c mice to select for tumorogenicity. For challenge, mice were injected intradermally with $10^6$ Meth A cells. Tumor growth was observed for eight weeks. Rejection was scored as the disappearance of the tumor mass within 20 days after tumor challenge.

(b) The 3LL-tumor (Eisenbach et al., 1983) is a metastasing lung, carcinoma cell line of C57BL/6 origin, that constitutively overexpresses p53, mostly wild-type. The cells were grown in DMEM containing 10% heat-inactivated fetal calf serum (FCS).

(iv) Immunization

Mice were immunized intradermally in the hind footpads with 20 μg of mAb in PBS in a 100 μl emulsion 1:1 in Complete Freund's Adjuvant (CFA; Difco Laboratories, Detroit, Mich.). An intradermal booster injection with 20 μg of the mAb in PBS alone was given three weeks later. Mice were bled at different times after the boost, and the sera were tested for specific antibodies.

(v) Recombinant p53 Proteins

E Coli BL21 (DE3) cells transformed with the T7 expression vector containing regularly spliced mouse p53 cDNA were used to express wild type or mutant p53 as previously described (Shohat-Foord et at., 1991; Wolkowicz et al., 1995). For protein induction, IPTG at a final concentration of 0.4 mm was added when the cells had reached an $O.D._{600}$ of 0.8-1.0. Three hours after induction, the cells were harvested from a 200 ml culture by centrifugation, and the pellet was resuspended in 5 ml of ice-cold lysis buffer (20 mM Tris-HCl, pH: 7.4; 500 mM NaCl; 10% glycerol; 1 mM EDTA; 1 mM PMSF; 5 μg/ml leupeptine; 10 μg/ml aprotinin and 0.1% NP40). The lysate was subjected to sonication for 10 cycles of 15 s of sonication followed by 15 s of gentle swirling. The solicited sample was subjected to two cycles of freeze-thaw and then centrifuged for 10 min at 10.000×g. The supernatant was diluted with an equal volume of ice-cold water and an equal volume of saturated ammonium sulfate was added drop-wise to obtain a final concentration of 33% saturated ammonium sulfate. After 15 min on ice and centrifugation, the pellet was resuspended in 1 ml of lysis buffer and centrifuged for 5 min at 4° C. The supernatant was diluted with 4 ml of lysis buffer devoid of NaCl. Wild type p53 and mutant p53 were translated in vitro using Bluescript plasmids carrying the specific cDNA (Promega, Madison, Wis.).

(vi) Antibody Assays

Antibodies to DNA or to p53 were detected using three different assay systems. (i) immunoprecipitation was used to detect antibodies to wild-type and mutant p53, as described (Wolkowicz et al., 1995; (ii) gel-retardation was used to detect antibodies to the synthetic oligonucleotide consensus sequence specific for p53 (Wolkowicz et al., 1995); and (iv) ELISA was done according to Waisman et al., 1993, using anti-mouse IgG and IgG1, IgG2a and IgG2b specific reagents to detect IgG antibody isotypes (Elias et al., 1997).

(vii) Cloning and Sequencing of Immunoglobulin H and L Chains

The polymerase chain reaction (PCR) was used to amplify mAb cDNA as described (Sambrook et al., 1989). Briefly, forward primers located in the constant region or in the J region and backward primers located in the V region, were used for amplification using Taq DNA polymerase s (Promega, Madison, Wis., USA). The primers used for the PCR were described by Orlandi et al., 1989.

The PCR product was cloned, and ligated DNA was inserted into competent bacterial cells. Positive colonies were picked using specific internal primers that were labeled with g-ATP. Positive clones were grown and ssDNA was prepared as described (Sambrook et al., 1989). The ssDNA was sequenced using the Sequenase 2.0 kit (USB).

PCR products were separated from the primers used for the reaction using Primer Remover (Advanced Genetic Technologies, MD, USA). Around 1200 ng DNA were used for each sequencing (Applied Biosystems). Sequences were analyzed using Applied Biosystems and GCG package programs.

(viii) Peptide Synthesis

Peptides were synthesized as described (Konen-Waisman et al., 1995). Briefly, peptides were prepared with an automated multiple peptide synthesizer (Abimed Model AMS 422; Langenfeld, Germany) using the company's protocols for N-α-fluorenylmethoxycarbonyl(Fmoc) synthesis, or were prepared manually by a standard solid phase method (Merrifield, 1963) employing either N-α-Fmoc or N-α-t-butyloxycarbonyl (t-Boc) strategies. Crude products were purified by reversed phase HPLC on a semi-preparative C8-column (Lichrosorb RP-8, 7 250×10 mm, Merck, Darmstadt, Germany). Elution of peptides was achieved by linear gradients established between 0.1% trifluoroacetic acid (TFA) in water and 0.1% TFA in 75% acetonitrile in 25 water (v/v). The purity of the single peptide products was ascertained by analytical reversed-phase HPLC and amino acid analysis.

Example 1

Induction of Anti-p53 Immunity

To exploit the idiotypic network to induce immunity to the p53 protein, BALB/c mice were unimmunized or were immunized with control mAb 9E10, or with anti-mutant p53 mAb 240 or anti-native p53 mAb 246. Ten days after the boost, the mice were bled and the sera were tested for antibodies to native p53 or mutated p53 by an ELISA assay, or by a precipitation assay. Antibodies were measured after booster immurdzation.

For the ELISA assay flat bottom maxi-sorb plates (Nunc, Roskilde, Denmark) were coated with 50 μl per well of mutant or wild type p53 at a concentration of 10 μg/ml. After incubation with antigen, the plates were washed and blocked over night with 5% fetal calf serum (FCS; BioLab, Jerusalem, Israel) or with 1% bovine serum albumin (BSA; Sigma) in PBS. Test sera diluted serially (1/50 to 1/800) were then added for 90 min, followed by incubation for 75 min with 50 μl per well of alkaline phosphatase-conjugated goat anti-mouse IgG, $F_c$ fragment (Jackson Immunoresearch Laboratories, Inc. West Grove, Pa.). After washing, the plates were incubated with the substrate, p-nitrophenil phosphate disodium (Sigma) and read using an ELISA reader at 405 nm. Sera manifesting an O.D. reading, after substraction of the background, of 0.3 or greater, were scored as positive.

For the immunoprecipitation assay, TCA-insoluble fraction of recombinant wild type or mutant p53 or lysates of Meth A tumor cells known to produce mutant p53 (Arai et al., 1986) metabolically labeled with $^{35}$S-methionine, were reacted with antibodies or test sera for 2 h at 4° C. The immune complexes were precipitated with Sepharose Protein A, separated on SDS-PAGE, electrotransferred to nitrocellulose membranes, and the proteins were detected using the Protoblot western blot Ap system (Promega, Madison, Wis.).

The results, summarized in Table 1, show that unimmunized control mice and mice immunized with control mAb 9E10 were not positive for anti-p53 antibodies. In contrast, mice immunized with anti-mutated p53 mAb 240 showed antibodies to both the mutated and native forms of p53. Mice immunized with anti-wild type p53 mAb 246 were positive for anti-p53 antibodies to wild type p53 but not to mutated p53. Analysis of the isotypes of the anti-p53 antibodies using the ELISA assay indicated that the antibodies included those of the IgG2a isotype regulated by T-helper 1 type cells that secrete interferon gamma (IFN-γ; Elias et al., 1997).

TABLE 1

Mice Immunized with anti-p53 mAb Develop Immune Reponses to p53

| | Antibody Assay | |
|---|---|---|
| Immunogen | Antigen | Incidence of Positive Mice |
| None | p53 | 0/20 |
| | mutated 53 | 0/20 |
| mAb 9E10 | p53 | 0/20 |
| | mutated p53 | 0/20 |
| mAb 240 | p53 | 10/10* |
| | mutated p53 | 10/10* |
| mAb 246 | p53 | 10/10* |
| | mutated p53 | 0/10 |
| mAb 421 | P53 | 10/10* |
| | mutated p53 | 10/10* |

*p < 0.01

FIG. 1 shows the retardation in gel of the p53-specific oligonucleotide sequence by anti-DNA antibodies developing only in the mice immunized with mAb 246, but not with mAb 240, mAb 421, mAb 9E10 or mAb R73. This result indicates that anti-DNA antibodies may recognize specific sequences of DNA.

Figure 2A:
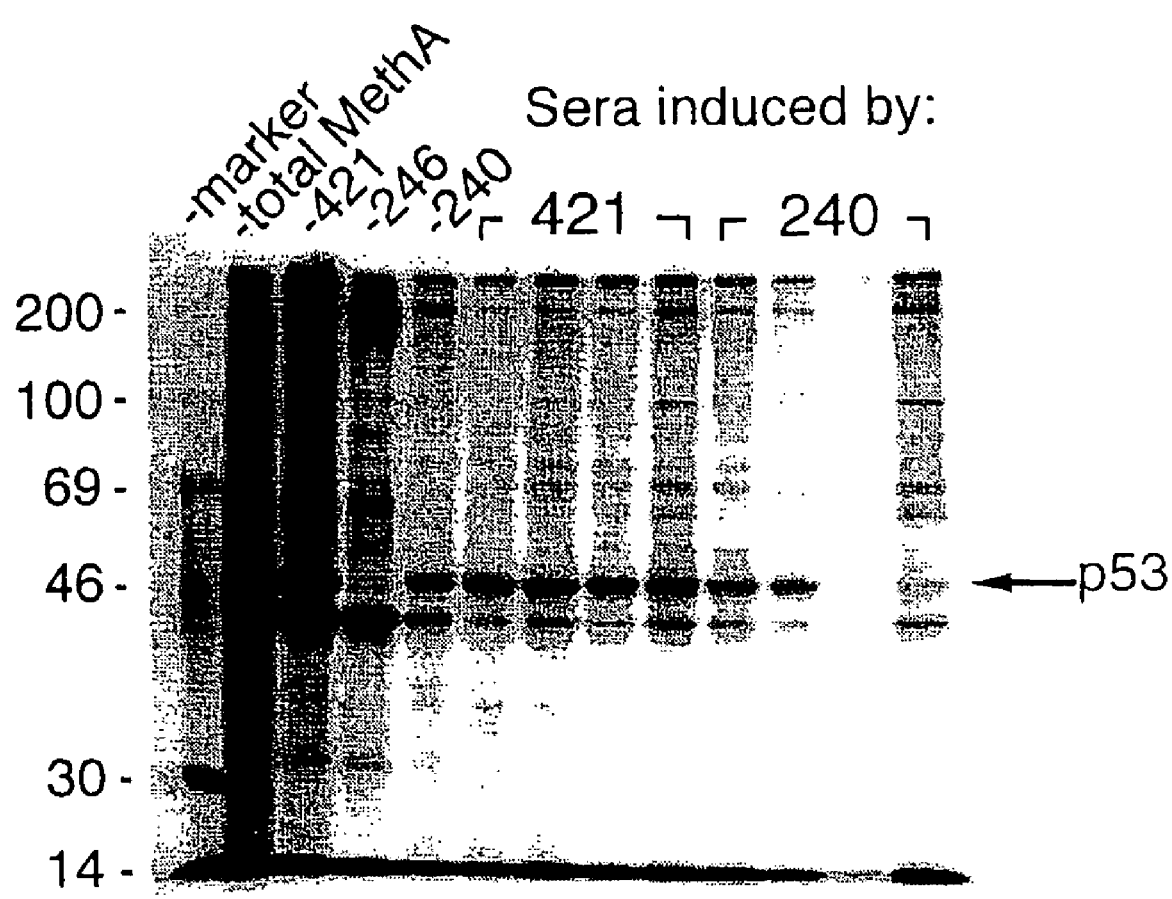

FIG. 2 shows a precipitation assay using an extract of the Meth A tumor metabolically labeled with $S^{35}$. This tumor produces mutant p53. It can be seen that mAb 240 (anti-mutant p53) precipitated the mutant p53 band, while mAb 246 did not precipitate the mutant p53 band, but did precipitate wild-type p53 (not shown). The mice immunized with mAb 421 or with mAb 240 developed specific anti-p53 antibodies. The mice immunized with mAb 246 or with mAb 9E10 did not develop antibodies to mutant p53. Immunoprecipitation of recombinant p53 confirmed these results.

Example 2

Immunized Mice Reject Tumors

Antibodies to tumor antigens have not been found to be effective in rejecting solid tumors (LoBuglio and Saleh, 1992; Mellstedt et al., 1991; Velders et al., 1995). To learn whether immunization with anti-p53 mAb might influence in vivo the development of a tumor bearing a mutated form of the p53 molecule, groups of BALB/c female mice were immunized as above with either mAb 240, mAb 246, mAb 421 or mAb 9E 10. The mice were challenged intradermally with $10^6$ Meth A tumor cells 10 days after the boost. Non-immunized mice were also tested. The results in Table 2 are expressed as the incidence of the mice that rejected the tumor in comparison to the mice that did not reject the tumor.

TABLE 2

Immunization with anti-p53 mAbs activates rejection of Meth A Sarcoma Cells

| Immunogen | Incidence of Rejected Tumors |
|---|---|
| None | 0/30 |
| mAb 240 | 9/10* |
| mAb 246 | 9/10* |
| mAb 421 | 9/10* |
| mAb9E10 | 0/10 |

*P < 0.01 compared to non-immunized control mice (none)

Table 3 summarizes the antibody results and also shows that the mice that anti-p53 antibodies also rejected the Meth A tumor. The tumor rejection experiments have been repeated 4 times and have involved 30-40 mice per group. About 90% of the mice developing p53 immunity rejected their tumors. It is quite possible that T cells were involved in the rejection process. However, it has been shown that intact antibodies can enter living cells (Alarcon-Segovia et al., 1996; Madaio et al., 1996; Yanase et al., 1994; Ma et, al., 1991) and it is conceivable that the anti-p53) antibodies themselves killed the tumor cells, possibly by inducing apoptosis (Madaio et al., 1996). It is also possible that the anti-p53 mAbs exerted an anti-tumor effect through antibody-dependent cytotoxicity (ADCC). The antibodies may also have acted in synergy with T cells (see Vasovic et al., 1997).

The growth of the Meth A tumor cells was inhibited in mice immunized with mAb 240, mAb 421 or mAb 246. In contrast to the protection induced by these mAbs, no protection was induced by immunization to control mAb 9E10. Thus, resistance to tumorchallenge was associated with the anti-p53 mAbs.

It can thus be summarized from the above results that immunization with anti-p53 mAb molecules induces anti-p53 immunity and can induce anti-DNA antibodies. The anti-DNA antibodies can show specificity for-DNA recognized by different p53 domains. The anti-p53 autoimmunity is associated with tumor rejection. These results are summarized in Table 3.

TABLE 3

Immunization to Anti-p53 mAb Molecules Induces Specific Anti-DNA and Anti-p53 Immunity. The Anti-p53 Immunity Is Associated with Tumor Rejection

| | | Induced Reactivities | | |
|---|---|---|---|---|
| mAb | Specificity | Anti-DNA Specific for the p53 Reactive Sequence | anti-p53 | Tumor Rejection |
| 9E10 | Myc | No | No | No |
| 240 | mutated p53 | No | Yes | Yes |
| 246 | p53-specific domain | Yes | Yes | Yes |
| 421 | p53-carboxy domain | No | Yes | Yes |

Although antibodies naturally arising in tumor patients to the amino-terminal domain of p53) are not protective and may even indicate a poor prognosis (Schlichtholz et al., 1992), the rejection of tumors by mAb treatment may be explained by the fact that the mAbs were specific for other domains of p53. Moreover, the generation of IgG antibodies by the mAb treatment suggests that T cells may be involved. Be that as it may, the induction of anti-p53 reactivity by the use of specific mAbs is functionally effective.

Example 3

Preparation of CDR-Based Peptides of Anti-P53mAbs

The light (L) and heavy (H) chains of the anti-p53 mAbs 240, 246, 248 and 421 were cloned and sequenced as described in Materials and Methods, section vii. The sequences are shown in FIG. 3 (CDR sequences are underlined).

Peptides V-IX described hereinabove were synthesized as described in Materials and Methods, section viii.

Example 4

CDR-Based Peptides of Anti-p53 mAbs Induce Anti-p53 Immunity in Mice

Immunization of BALB/c mice with peptides V-IX of Example 3 was carried out as described for the whole mAbs in Materials and Methods, section iv, using 100 μg of peptide, and then assayed for the development of anti-p53 antibodies.

The incidence of mice developing IgG anti-p53 antibodies (ELISA assay) was 8/10 and 7/10 for peptides V and VI, the CDR3-based peptides of mAb 240 and mAb 421, respectively.

The results of another experiment carried out with peptides V-IX (Table 4) show that mice immunized with these peptides rejected the Meth A tumor.

TABLE 4

Rejection of Meth A Tumor in Mice Immunized with Anti-p53 mAb CDR-Based Peptides V-IX

| Peptide Immunogen | Incidence of Rejected Tumors |
|---|---|
| None | 0/5 |
| V | 4/5 |
| VI | 5/5 |
| VII | 5/5 |
| VIII | 4/5 |
| IX | 4/5 |

These experiments show that fragments of anti-p53 mAb, e.g. CDR-based peptides, can be used to induce anti-p53 immunity.

Example 5

Prevention of Lung Carcinoma Metastasis by Immunization with Monoclonal Antibodies to p53

Since the most likely application for immunotherapy of tumor is not only the treatment of solid tumors, but rather the treatment of metastasis after surgical removal of a solid tumor, the anti-p53 mAbs were also applied in a model of a metastasing tumor.

Figure 4:
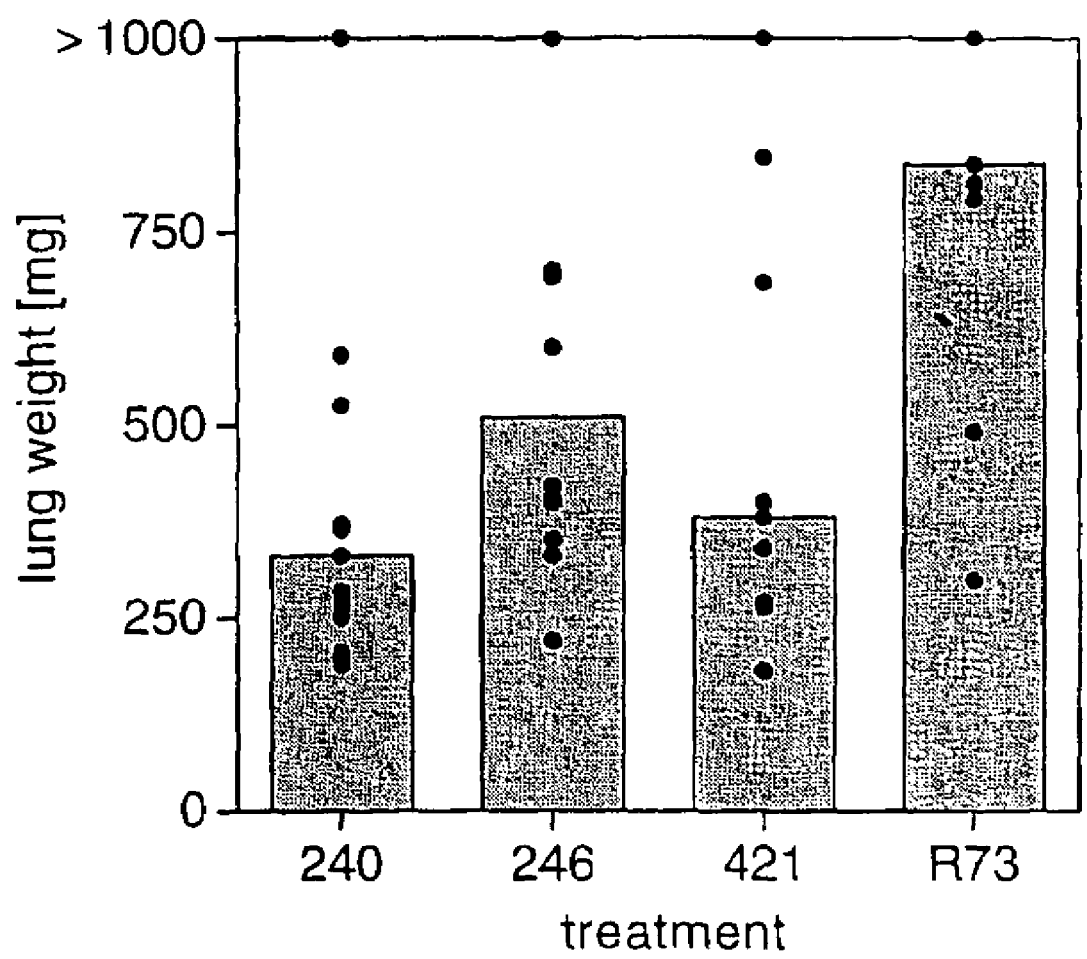
FIG. 4 shows the protective effect of immunizing mice with the anti-p53 mAbs 240, 246 and 421 against the development of lung carcinoma metastasis in mice. mAb R73 was used as a control immunogen. Dots indicate the weight of individual lungs, bars the median of each group. Normal lung weight is around 200 mg.

Immunization of C57BL/6 mice was performed with anti-p53 mabs 240, 246, 421 and mAb R73 as control, as described in Materials and Methods, section (iv). Ten days after the boost, the mice were injected intradermally in the hind footpads with $2 \times 10^5$ 3LL-lung carcinoma cells. Tumor growth at the injection site was observed. The tumors were excised when they reached 8 mm. The mice were sacrificed 21 days after tumor removal and their lungs were weighed as a quantitative measure of the metastatic load. In case of spontaneous mortality, the lung weight was determined on the day of death. FIG. 4 shows the protective effect of the p53 antibodies against the development of lung metastasis. All three anti-p53 mAbs tested significantly protected the 3LL-challenged mice against metastasis ($p<0.01$, when compared to R73).

REFERENCES

Alarcon-Segovia et al, "Broken dogma: penetration of autoantibodies into living cells", *Immunology Today* 17:163-164 (1996)

Alzrl et al, "Three-dimensional structure of antibodies", *Ann Rev Immunol* 6:555-580 (1988)

Arai et al, "Immunologically distinct p53 molecules generated by alternative splicing" *Mol Cell Biol* 6:3232-3239 (1986)

Bruggemann et al, "The immunogenicity of chimeric antibodies", *J Exp Med* 170:2153-2157 (1989)

Cazenave P A, "Idiotypic-anti-idiotypic regulation of antibody synthesis in rabbits", *Proc Natl Acad Sci USA* 74:5122-5125 (1977)

Cohen I R, "Natural Id-anti-Id networks and the immunological homunculus", in *Theories of Immune Networks*, Atlan et al eds (Heidelberg: Springer-Verlag), pp. 6-12 (1989)

Cohen I R, "The cognitive paradigm and the immunological homuncuius", *Immunol Today* 13:490-494 (1992)

Eisenbach et al, "MHC imbalance and metastatic spread in Lewis lung carcinoma clones", *Int J Cancer* 32:113-120 (1983)

Elias et al, "Hsp60 peptide therapy of NOD mouse diabetes induces a Th2 cytokine burst and down-regulates autoinimunity to various B-cell antigens", *Diabetes* 46:758-764 (1997)

el-Deiry "Definition of a consensus binding site for p53", *Nature Genet* 1(4):5-49 (1992)

Gannon et al, "Activating mutations in p53 produce a common conformational effect. A monoclonal antibody specific for the mutant form", *EMBO J.* 9:1595-1602 (1990)

Harlow et al, "Monoclonal antibodies specific for simian virus 40 tumor antigens", *J Virol* 39:861-869 (1981)

Hollstein et al, "p53 mutations in human cancers. *Science* 253:49-53 (1991)

Houbiers et al, "In vitro induction of human cytotoxic T lymphocyte responses against peptides of mutant and wild-type p53", *Eur J Immunol* 23:2072-2077 (1993)

Hunig et al, "A monoclonal antibody to a constant determinant of the rat T cell antigen receptor that induces T cell activation. Differential reactivity with subsets of immature and mature T lymphocytes", *J Exp Med* 169:73-86 (1989)

Jerne N K, "Towards a network theory of the immune system", *Ann Inim (Paris)* 85:2260-2264 (1974)

Lee et al, "p53 and its 14 Kda C-terminal domain recognize primary DNA damage in the form of insertion/deletion", *Cell* 81:1013-1020 (1995)

LoBuglio et al, "Advances in monoclonal antibody therapy of cancer", *Am J Med Sci* 3(4):214-224 (1992)

Lubin et al, "Analysis of p53 30 antibodies in patients with various cancers define B-cell epitopes of human p53): distribution on primary structure and exposure on protein surface", *Cancer Res* 53:5872-5876 (1993)

Ma et al, "Antibody penetration of viable human cells. 1. Increased penetration of human lymphocytes by anti-RNP IgG", *Clin Exp Immunol* 84:833-891 (1991)

Madaio et al, "Spontaneously produced anti-DNA/DNase I autoantibodies modulate nuclear apoptosis in living cells. *Eur J Immunol* 26:3035-3041 (1996)

Melief et al, "T-cell immunotherapy of cancer", *Res Immunol* 142:425-429 (1991)

Mellstedt", "The therapeutic use of monoclonal antibodies in colorectal carcinoma", *Semin Oncol* 18:462-477 (1991)

Moll et al, "Wild-type p53 protein undergoes cytoplasmic sequestration in undifferentiated neuroblastomas but not in differentiated tumors", *Proc Natl Acad Sci USA* 92:4407-4411 (1995)

Mozes et al, "Direct binding of a myasthenia gravis related epitope to MHC class II molecules on living murine antigen-presenting cells", *EMBO J.* 8:4049-4052 (1989)

Munro et al, "An Hsp70-like protein in the ER: identity with the 78 kd glucose-regulated protein and immunoglobulin heavy chain binding protein", *Cell* 46:291-300 (1986)

Nisonoff A, "Idiotypes: concepts and applications", *J Immunol* 147:2429-2438 (1991)

Noguchi et al, "A mouse mutant p53) product recognized by CD4+ and CD8+ T cells", *Proc Natl Acad Sci USA* 91:3171-3175 (1994)

Noguchi et al, "Influence of interleukin 12 on p53 peptide vaccination against established Meth A sarcoma", *Proc Natl Acad Sci USA* 92:2219-2223 (1995)

Old et al, *Ann NY Acad Sci* 101:80-106 (1962)

Orlandi et al, "Cloning immunoglobulin domains for expression by the polymerase chain reaction", *Proc Natl Acad Sci USA* 86:3833-3837 1989

Sambrook et al, *Molecular Cloning: A. Laboratory Manual*, 2nd ed., Cold Spring Harbor Press (1989)

Schlichtholz et al, "The immune response to p53) in breast cancer patients is directed against immunodominant epitopes unrelated to the mutational hot spot", *Cancer Res* 52:6380-6384 (1992)

Shohat-Foord et al, "A DNA binding domain is contained in the C-terminus of wild type p53) protein", *Nucleic Acid Res* 19:5191-5198 (1991)

Soussi T, "The humoral response to the tumor suppressor gene product p53) in human cancer. Implications for diagnosis and therapy", *Immunol Today* 17:354-356 (1996)

Stevenson et al, "Idiotypic DNA vaccines against B-cell lymphoma", *Immunol Rev* 211-228 (1995)

Takemori et al, "The immune response against anti-idiotope antibodies. I. Induction of idiotope-bearing antibodies and analysis of the idiotope repertoire", *Eur J Immunol* 12:1040-1046 (1982)

Tilkin et al, "Primary proliferative T cell response to wild-type p53 protein in patients with breast cancer", *Eur J Immunol* 25:1765-1769 (1995)

Urbain et al, "Idiotypic regulation of the immune system by the induction of antibodies against anti-idiotypic antibodies", *Proc Natl Acad Sci USA* 74:5126-5130 (1977)

Vasovic et al, Sinergy between an antibody and CD8+ cells in eliminating an established tumor", *Eur J Immunol* 27:3374-382 (1997)

Velders et al, "Immunotherapy with low and high affinity monoclonal antibodies 17-IA and 323/A3 in a nude mouse xenograft carcinoma model", *Cancer Res* 55:43198-4403 (1995)

Vile et al, "Gene transfer technologies for the gene therapy of cancer", *Gene Therapy* 1:88-98 (1994)

Waisman et al, "The role of the 16/6 idiotype network in the induction and manifestations of systemic lupus erythematosus", *Int Immunol* 5:1293-1310 (1993)

Wettendorff et al, "Modulation of antitumor immunity by anti-idiotypic antibodies" in *Idiotypic Network and Diseases*, Cerny et al (eds.), American Society for Microbiology, Washington, D.C. pp 203-229 (1990)

Wolkowicz et al, "The DNA binding activity of wild type p53 is modulated by blocking its various antigenic epitopes", *Oncogene* 10:1167-1174 (1995)

Yanase et al, "A subgroup of murine monoclonal anti-deoxyribonucleic acid antibodies traverse the cytoplasm and enter the nucleus in a time- and temperature-dependent manner", *Lab Investigation* 71:52-60 (1994)

Yanuck et al, "A mutant p53 tumor suppressor protein is a target for peptide-induced CD8+ cytotoxic T-cells", *Cancer Res* 53:3257-3261 (1993)

Yefenof et al, "Induction of B cell tumor dormancy by anti-idiotypic antibodies", *Curr Opinion Immunol* 5:740-744 (1993)

Yewdell et al, "Monoclonal antibody analysis of p53 expression in normal and transformed cells", *J Virol* 59:444-452 (1986)

Zambetti et al, "A comparison of the biological activities of wild-type and mutant p53", *FASEB J* 7:855-865 (1993)

---

What is claimed is:

1. A method for activating an enhanced anti-tumor immune response in a mammal comprising:
   determining at least one immunogen that can elicit antibodies to p53 wherein the immunogen is a synthetic peptide which is 7-30 amino acids in length and contains a sequence of a CDR of the heavy or light chain of an anti-p53 mAb or a salt thereof; and
   administering an effective amount of the at least one immunogen to a mammal having a tumor characterized by mutation, over-expression or accumulation of p53.

2. The method according to claim 1, wherein the method is used for induction of immune responses to mutated and wild-type forms of p53 in the mammal.

3. The method according to claim 1, wherein the peptide contains a sequence of the CDR2 or CDR3 of the heavy chain, or of the CDR3 of the light chain, of an anti-p53 mAb.

4. The method according to claim 3, wherein the sequence of the CDR is selected from mAb 240, 246 and 421.

5. The method according to claim 4, wherein the peptide is selected from the group consisting of:
   (i) peptides, herein designated Ia-Ib, based on the CDR2 and CDR3, respectively, of the heavy chain (240VH), and peptide Ic based on the CDR3 of the light chain (240VL), of the anti-p53 mAb 240, of the sequences: (Ia) Glu-Ile-Asp-Pro-Ser-Asp-Ser-Tyr-Thr-Asn-Tyr-Asn-Gln-Asn-Phe-Lys-Asp (SEQ ID NO:9), (Ib) Leu-Leu-Arg-Tyr-Phe-Ala-Met-Asp-Tyr (SEQ ID NO:10), or (Ic) Gln-His-Ile-Arg-Glu-Leu-Thr-Arg (SEQ ID NO:11);
   (ii) peptides, herein designated IIa-IIb, based on the CDR2 and CDR3, respectively, of the heavy chain (246VH), and peptide IIc based on the CDR3 of the light chain (246VL), of the anti-p53 mAb 246, of the sequences: (IIa) Asp-Ile-Asn-Pro-Asn-Asn-Gly-Tyr-Thr-Ile-Tyr-Asn-Gln-Lys-Val-Lys-Gly (SEQ ID NO:12), (IIb) Gly-Gly-Gly-Leu-Lys-Gly-Tyr-Pro-Phe-Val-Tyr (SEQ ID NO:13), or (IIc) Gln-Gln-Arg-Ser-Ser-Phe-Pro-Phe-Thr (SEQ ID NO:14); and
   (iii) peptides, herein designated IVa-IVb, based on the CDR2 and CDR3, respectively, of the heavy chain (421VH), and peptide IVc based on the CDR3 of the light chain (421VL), of the anti-p53 mAb 421, of the sequences: (IVa) Trp-Ile-Asp-Pro-Glu-Asn-Gly-Asp-Thr-Glu-Tyr-Ala-Pro-Lys-Phe-Gln-Gly (SEQ ID NO:18), (IVb) Tyr-Gly-Asp-Ala-Leu-Asp-Tyr (SEQ ID NO:19), or (IVc) Trp-Gln-Gly-Thr-His-Ser-Pro-Leu-Thr (SEQ ID NO:20); and
   salts thereof.

6. The method according to claim 4, wherein the peptide contains a sequence selected from the group of sequences consisting of Ic (SEQ ID NO:11), IIa (SEQ ID NO:12), and IVc (SEQ ID NO:20).

7. The method according to claim 6, wherein the peptide is selected from the group consisting of peptides V-VII of the sequences:
   Peptide V: Tyr-Tyr-Cys-Gln-His-Ile-Arg-Glu-Leu-Thr-Arg-Ser-Glu-Gly-Gly-Pro-Ser (SEQ ID NO:21),
   Peptide VI: Gly-Val-Tyr-Tyr-Cys-Trp-Gln-Gly-Thr-His-Ser-Pro-Leu-Thr-Phe-Gly-Ala-Gly-Thr-Lys (SEQ ID NO:22), and
   Peptide VII: Gly-Asp-Ile-Asn-Pro-Asn-Asn-Gly-Tyr-Thr-Ile-Tyr-Asn-Gln-Lys-Val-Lys-Gly-Lys-Ala (SEQ ID NO:23), and
   salts thereof.

8. The method according to claim 1, wherein the peptide contains the sequence: Gln-His-Ile-Arg-Glu-Leu-Thr-Arg (SEQ ID NO:11) or Tyr-Tyr-Cys-Gln-His-Ile-Arg-Glu-Leu-Thr-Arg-Ser-Glu-Gly-Gly-Pro-Ser (SEQ ID NO:21).

9. The method according to claim 1, wherein the peptide is in the form of an organic or inorganic salt.

10. The method according to claim 1, wherein the peptide is administered in the form of a pharmaceutical composition comprising the peptide and a pharmaceutically acceptable carrier.

11. The method according to claim 1, which further comprises administering to a patient effective amounts of at least one different peptide containing a sequence of the same or different CDRs of the same anti-p53 mAb or of different anti-p53 mAbs.

12. The method according to claim 1, wherein the peptide is obtained by a process which comprises:
 identifying a first monoclonal anti-p53 antibody capable of generating anti-idiotope anti-p53 antibodies in a subject immunized with the first antibody;
 identifying at least one sequence of a CDR of the first anti-p53 mAb, wherein the sequence is a CDR2 or CDR3 of the heavy chain of the first anti-p53 mAb, or the CDR3 of the light chain of the first anti-p53 mAb; and
 synthesizing peptides or salts thereof that contain the CDR sequence such that the peptides, or salts, thereof are capable of eliciting antibodies to p53 upon administration to a subject.

13. A method for activating an enhanced immune response to p53 in a mammal that is afflicted with a tumor characterized by mutation, overexpression or accumulation of p53 comprising
 determining at least one immunogen that can elicit antibodies to p53 wherein the immunogen is a synthetic peptide which is 7-30 amino acids in length and contains a sequence of a CDR of the heavy or light chain of an anti-p53 mAb or a salt thereof; and
 immunizing the mammal by administering an effective amount of the at least one immunogen.

14. The method according to claim 13, wherein the method induces an immune responses to a mutated or wild-type form of p53 in the mammal.

15. The method according to claim 14, wherein the peptide contains a sequence of the CDR2 or CDR3 of the heavy chain, or of the CDR3 of the light chain, of an anti-p53 mAb.

16. The method according to claim 15, wherein the sequence of the CDR is selected from mAb 240, 246 and 421.

17. The method according to claim 16, wherein the peptide is selected from the group consisting of:
 (i) peptides, herein designated Ia-Ib, based on the CDR2 and CDR3, respectively, of the heavy chain (240VH), and pepticle Ic based on the CDR3 of the light chain (240VL), of the anti-p53 mAb 240, of the sequences:
  (Ia) Glu-Ile-Asp-Pro-Ser-Asp-Ser-Tyr-Thr-Asn-Tyr-Asn-Gln-Asn-Phe-Lys-Asp (SEQ ID NO:9), (Ib) Leu-Leu-Arg-Tyr-Phe-Ala-Met-Asp-Tyr (SEQ ID NO:10), or (Ic) Gln-His-Ile-Arg-Glu-Leu-Thr-Arg (SEQ ID NO:11);
 (ii) peptides, herein designated IIa-IIb, based on the CDR2 and CDR3, respectively, of the heavy chain (246VH), and peptide 11c based on the CDR3 of the light chain (246VL), of the anti-p53 mAb 246, of the sequences: (IIa) Asp-Ile-Asn-Pro-Asn-Asn-Gly-Tyr-Thr-Ile-Tyr-Asn-Gln-Lys-Val-Lys-Gly (SEQ ID NO:12), (IIb) Gly-Gly-Gly-Leu-Lys-Gly-Tyr-Pro-Phe-Val-Tyr (SEQ ID NO:13), or (IIc) Gln-Gln-Arg-Ser-Ser-Phe-Pro-Phe-Thr (SEQ ID NO:14); and
 (iii) peptides, herein designated IVa-IVb, based on the CDR2 and CDR3, respectively, of the heavy chain (421VH), and peptide IVc based on the CDR3 of the light chain (421VL), of the anti-p53 mAb 421, of the sequences: (IVa) Trp-Ile-Asp-Pro-Glu-Asn-Gly-Asp-Thr-Glu-Tyr-Ala-Pro-Lys-Phe-Gln-Gly (SEQ ID NO:18), (IVb) Tyr-Gly-Asp-Ala-Leu-Asp-Tyr (SEQ ID NO:19), or (IVc) Trp-Gln-Gly-Thr-His-Ser-Pro-Leu-Thr (SEQ ID NO:20); and
 salts thereof.

18. The method according to claim 16, wherein the peptide contains a sequence selected from the group of sequences consisting of Ic (SEQ ID NO:11), IIa (SEQ ID NO:12), and IVc (SEQ ID NO:20).

19. The method according to claim 18, wherein the peptide is selected from the group consisting of peptides V-VII of the sequences:
 Peptide V: Tyr-Tyr-Cys-Gln-His-Ile-Arg-Glu-Leu-Thr-Arg-Ser-Glu-Gly-Gly-Pro-Ser (SEQ ID NO:21),
 Peptide VI: Gly-Val-Tyr-Tyr-Cys-Trp-Gln-Gly-Thr-His-Ser-Pro-Leu-Thr-Phe-Gly-Ala-Gly-Thr-Lys (SEQ ID NO:22), and
 Peptide VII: Gly-Asp-Ile-Asn-Pro-Asn-Asn-Gly-Tyr-Thr-Ile-Tyr-Asn-Gln-Lys-Val-Lys-Gly-Lys-Ala (SEQ ID NO:23), and
 salts thereof.

20. The method according to claim 13, wherein the peptide contains the sequence: Gln-His-Ile-Arg-Glu-Leu-Thr-Arg (SEQ ID NO:11) or Tyr-Tyr-Cys-Gln-His-Ile-Arg-Glu-Leu-Thr-Arg-Ser-Glu-Gly-Gly-Pro-Ser (SEQ ID NO:21).

21. The method according to claim 13, wherein the peptide is in the form of an organic or inorganic salt.

22. The method according to claim 13, wherein the peptide is administered in the form of a pharmaceutical composition comprising the peptide and a pharmaceutically acceptable carrier.

23. The method according to claim 13, which further comprises administering to a patient effective amounts of at least one different peptide containing a sequence of the same or different CDRs of the same anti-p53 mAb or of different anti-p53 mAbs.

24. The method according to claim 13, wherein the peptide is obtained by a process which comprises:
 identifying a first monoclonal anti-p53 antibody capable of generating anti-idiotope anti-p53 antibodies in a subject immunized with the first antibody;
 identifying at least one sequence of a CDR of the first anti-p53 mAb, wherein the sequence is a CDR2 or CDR3 of the heavy chain of the first anti-p53 mAb, or the CDR3 of the light chain of the first anti-p53 mAb; and
 synthesizing peptides or salts thereof that contain the CDR sequence such that the peptides, or salts, thereof are capable of eliciting antibodies to p53 upon administration to a subject.

* * * * *

UNITED STATES PATENT AND TRADEMARK OFFICE
CERTIFICATE OF CORRECTION

PATENT NO. : 7,378,092 B2 Page 1 of 1
APPLICATION NO. : 11/129359
DATED : May 27, 2008
INVENTOR(S) : Cohen et al.

It is certified that error appears in the above-identified patent and that said Letters Patent is hereby corrected as shown below:

<u>Column 31</u>:
Line 55, change "pepticle" to -- peptide --.

<u>Column 32</u>:
Line 12, change "Gin" to -- Gln --.

Signed and Sealed this

Fifth Day of August, 2008

JON W. DUDAS
*Director of the United States Patent and Trademark Office*

SEQUENCE LISTING

```
<160> NUMBER OF SEQ ID NOS: 25

<210> SEQ ID NO 1
<211> LENGTH: 104
<212> TYPE: PRT
<213> ORGANISM: Mus musculus

<400> SEQUENCE: 1

Ala Thr Gly Glu Ala Gly Ala Ser Val Lys Leu Ser Cys Lys Ala Ser
 1               5                  10                  15

Gly Tyr Thr Phe Thr Ser Ser Trp Ile Asn Trp Val Lys Gln Arg Pro
            20                  25                  30

Gly Gln Gly Leu Glu Trp Ile Gly Glu Ile Asp Pro Ser Asp Ser Tyr
        35                  40                  45

Thr Asn Tyr Asn Gln Asn Phe Lys Asp Lys Ala Thr Leu Thr Val Asp
    50                  55                  60
```

```
Lys Ser Ser Ser Thr Ala Tyr Met Gln Leu Ser Ser Leu Thr Ser Glu
 65                  70                  75                  80

Asp Ser Ala Val Tyr Tyr Cys Ala Arg Leu Leu Arg Tyr Phe Ala Met
                 85                  90                  95

Asp Tyr Trp Gly Gln Gly Thr Thr
            100

<210> SEQ ID NO 2
<211> LENGTH: 103
<212> TYPE: PRT
<213> ORGANISM: Mus musculus

<400> SEQUENCE: 2

Phe Leu Ser Cys Ile Ser Gly Ala Glu Gly His His Leu Ile Gln Gly
 1               5                  10                  15

Gln Gln Lys Cys Gln Tyr Ile Trp Leu Tyr Tyr Met His Trp Asn Gln
             20                  25                  30

Gln Lys Pro Gly Gln Pro Arg Leu Leu Ile Tyr Leu Val Ser Asn
             35                  40                  45

Leu Glu Ser Gly Val Pro Ala Arg Phe Ser Gly Ser Gly Ser Gly Thr
 50                  55                  60

Asp Phe Thr Leu Asn Ile His Pro Val Glu Glu Asp Ala Ala Thr
 65                  70                  75                  80

Tyr Tyr Cys Gln His Ile Arg Glu Leu Thr Arg Ser Glu Gly Gly Pro
                 85                  90                  95

Ser Trp Arg Ser Ile Arg Ile
            100

<210> SEQ ID NO 3
<211> LENGTH: 106
<212> TYPE: PRT
<213> ORGANISM: Mus musculus

<400> SEQUENCE: 3

Ser Trp Val Lys Pro Gly Ala Ser Val Lys Ile Pro Cys Lys Ala Ser
 1               5                  10                  15

Gly Tyr Thr Phe Thr Asp Tyr Asn Met Asp Trp Val Lys Gln Ser His
             20                  25                  30

Gly Lys Ser Leu Glu Trp Ile Gly Asp Ile Asn Pro Asn Asn Gly Tyr
             35                  40                  45

Thr Ile Tyr Asn Gln Lys Val Lys Gly Lys Ala Thr Leu Thr Val Asp
 50                  55                  60

Lys Ser Ser Asn Thr Ala Tyr Met Glu Leu Arg Ser Leu Thr Ser Glu
 65                  70                  75                  80

Asp Thr Ala Val Tyr Tyr Cys Val Arg Gly Gly Leu Lys Gly Tyr
                 85                  90                  95

Pro Phe Val Tyr Trp Gly Gln Gly Thr Thr
            100                 105

<210> SEQ ID NO 4
<211> LENGTH: 92
<212> TYPE: PRT
<213> ORGANISM: Mus musculus
<220> FEATURE:
<221> NAME/KEY: misc_feature
<222> LOCATION: (53)..(53)
<223> OTHER INFORMATION: Xaa is any amino acid.
<220> FEATURE:
<221> NAME/KEY: misc_feature
```

```
<222> LOCATION: (86)..(86)
<223> OTHER INFORMATION: Xaa is any amino acid
<220> FEATURE:
<221> NAME/KEY: misc_feature
<222> LOCATION: (90)..(90)
<223> OTHER INFORMATION: Xaa is any amino acid

<400> SEQUENCE: 4

Lys Val Thr Ile Thr Cys Ser Ala Ser Ser Val Asn Phe Met His
1               5                   10                  15

Trp Phe Gln Gln Lys Pro Gly Thr Ser Pro Lys Leu Trp Ile Tyr Ser
            20                  25                  30

Thr Ser Asn Leu Ala Ser Gly Val Pro Ala Arg Phe Ile Gly Ser Gly
        35                  40                  45

Ser Gly Thr Ser Xaa Ser Leu Thr Ile Ser Arg Met Glu Ala Glu His
    50                  55                  60

Ala Ala Thr Tyr Tyr Cys Gln Gln Arg Ser Ser Phe Pro Phe Thr Tyr
65                  70                  75                  80

Gly Ser Gly Thr Lys Xaa Glu Ile Gln Xaa Asp Pro
                85                  90

<210> SEQ ID NO 5
<211> LENGTH: 111
<212> TYPE: PRT
<213> ORGANISM: Mus musculus

<400> SEQUENCE: 5

Leu Gln Glu Ser Gly Pro Glu Leu Val Lys Pro Gly Ala Ser Val Lys
1               5                   10                  15

Ile Ser Cys Lys Ala Ser Gly Tyr Thr Phe Thr Asp Tyr Tyr Met Asn
            20                  25                  30

Trp Val Lys Gln Ser His Gly Lys Ser Leu Glu Trp Ile Gly Asp Ile
        35                  40                  45

Tyr Pro Asn Asn Gly Phe Thr Tyr Asn Gln Lys Phe Lys Gly Lys
    50                  55                  60

Ala Thr Leu Thr Val Asp Lys Ser Ser Ser Thr Ala Tyr Asn Glu Leu
65                  70                  75                  80

Arg Asn Leu Thr Ser Glu Asp Ser Ala Val Tyr Tyr Cys Ala Arg Ser
                85                  90                  95

Gly Ser Arg Phe Asp Tyr Trp Gly Gln Gly Thr Thr Val His Arg
            100                 105                 110

<210> SEQ ID NO 6
<211> LENGTH: 109
<212> TYPE: PRT
<213> ORGANISM: Mus musculus

<400> SEQUENCE: 6

Met Asp Ile Gln Leu Thr Gln Ser Pro Ala Thr Leu Ser Val Thr Pro
1               5                   10                  15

Gly Asp Ser Val Ser Leu Ser Cys Arg Ala Ser Gln Ser Ile Ser Asn
            20                  25                  30

Asn Leu His Trp Tyr Gln Gln Lys Ser His Glu Ser Pro Arg Leu Leu
        35                  40                  45

Ile Lys Phe Ala Ser Gln Ser Ile Ser Gly Ile Pro Ser Arg Phe Ser
    50                  55                  60

Gly Ser Gly Ser Gly Thr Asp Phe Thr Leu Ser Ile Asn Ser Val Glu
65                  70                  75                  80
```

```
Thr Glu Asp Phe Gly Val Tyr Phe Cys Gln Gln Ser Asn Ser Trp Pro
            85                  90                  95

Val His Ala Arg Gly Gly Gly Thr Lys Leu Glu Asn Leu
            100                 105

<210> SEQ ID NO 7
<211> LENGTH: 112
<212> TYPE: PRT
<213> ORGANISM: Mus musculus

<400> SEQUENCE: 7

Leu Gln Glu Ser Gly Ala Glu Leu Val Arg Ser Gly Ala Ser Val Lys
1               5                   10                  15

Leu Ser Cys Thr Ala Ser Gly Phe Asn Ile Lys Asp Tyr Tyr Met His
            20                  25                  30

Trp Val Lys Gln Arg Pro Glu Gln Gly Leu Glu Trp Ile Gly Trp Ile
            35                  40                  45

Asp Pro Glu Asn Gly Asp Thr Glu Tyr Ala Pro Lys Phe Gln Gly Lys
        50                  55                  60

Ala Thr Met Thr Ala Asp Thr Ser Ser Asn Thr Ala Tyr Leu Gln Leu
65                  70                  75                  80

Ser Ser Leu Ala Ser Glu Asp Thr Ala Val Tyr Tyr Cys Asn Phe Tyr
            85                  90                  95

Gly Asp Ala Leu Asp Tyr Trp Gly Gln Gly Thr Thr Val Thr Val Ser
            100                 105                 110

<210> SEQ ID NO 8
<211> LENGTH: 112
<212> TYPE: PRT
<213> ORGANISM: Mus musculus

<400> SEQUENCE: 8

Pro Gln Asp Ile Gln Leu Thr Gln Ser Pro Leu Thr Leu Ser Val Thr
1               5                   10                  15

Ile Gly Gln Pro Ala Ser Ile Ser Cys Lys Ser Ser Gln Ser Leu Leu
            20                  25                  30

Asp Ser Asp Gly Lys Thr Tyr Leu Asn Trp Leu Leu Gln Arg Pro Gly
            35                  40                  45

Gln Ser Pro Lys Arg Leu Ile Tyr Leu Val Ser Lys Leu Asp Ser Gly
        50                  55                  60

Val Pro Asp Arg Phe Thr Gly Ser Gly Ser Gly Thr Asp Phe Thr Leu
65                  70                  75                  80

Lys Ile Asn Arg Val Glu Ala Glu Asp Leu Gly Val Tyr Tyr Cys Trp
            85                  90                  95

Gln Gly Thr His Ser Pro Leu Thr Phe Gly Ala Gly Thr Lys Leu Lys
            100                 105                 110

<210> SEQ ID NO 9
<211> LENGTH: 17
<212> TYPE: PRT
<213> ORGANISM: Mus musculus

<400> SEQUENCE: 9

Glu Ile Asp Pro Ser Asp Ser Tyr Thr Asn Tyr Asn Gln Asn Phe Lys
1               5                   10                  15

Asp

<210> SEQ ID NO 10
```

```
<211> LENGTH: 9
<212> TYPE: PRT
<213> ORGANISM: Mus musculus

<400> SEQUENCE: 10

Leu Leu Arg Tyr Phe Ala Met Asp Tyr
1               5

<210> SEQ ID NO 11
<211> LENGTH: 8
<212> TYPE: PRT
<213> ORGANISM: Mus musculus

<400> SEQUENCE: 11

Gln His Ile Arg Glu Leu Thr Arg
1               5

<210> SEQ ID NO 12
<211> LENGTH: 17
<212> TYPE: PRT
<213> ORGANISM: Mus musculus

<400> SEQUENCE: 12

Asp Ile Asn Pro Asn Asn Gly Tyr Thr Ile Tyr Asn Gln Lys Val Lys
1               5                   10                  15

Gly

<210> SEQ ID NO 13
<211> LENGTH: 11
<212> TYPE: PRT
<213> ORGANISM: Mus musculus

<400> SEQUENCE: 13

Gly Gly Gly Leu Lys Gly Tyr Pro Phe Val Tyr
1               5                   10

<210> SEQ ID NO 14
<211> LENGTH: 9
<212> TYPE: PRT
<213> ORGANISM: Mus musculus

<400> SEQUENCE: 14

Gln Gln Arg Ser Ser Phe Pro Phe Thr
1               5

<210> SEQ ID NO 15
<211> LENGTH: 17
<212> TYPE: PRT
<213> ORGANISM: Mus musculus

<400> SEQUENCE: 15

Asp Ile Tyr Pro Asn Asn Gly Phe Thr Thr Tyr Asn Gln Lys Phe Lys
1               5                   10                  15

Gly

<210> SEQ ID NO 16
<211> LENGTH: 7
<212> TYPE: PRT
<213> ORGANISM: Mus musculus

<400> SEQUENCE: 16

Ser Gly Ser Arg Phe Asp Tyr
1               5
```

```
<210> SEQ ID NO 17
<211> LENGTH: 10
<212> TYPE: PRT
<213> ORGANISM: Mus musculus

<400> SEQUENCE: 17

Gln Gln Ser Asn Ser Trp Pro Val His Ala
1               5                   10

<210> SEQ ID NO 18
<211> LENGTH: 17
<212> TYPE: PRT
<213> ORGANISM: Mus musculus

<400> SEQUENCE: 18

Trp Ile Asp Pro Glu Asn Gly Asp Thr Glu Tyr Ala Pro Lys Phe Gln
1               5                   10                  15

Gly

<210> SEQ ID NO 19
<211> LENGTH: 7
<212> TYPE: PRT
<213> ORGANISM: Mus musculus

<400> SEQUENCE: 19

Tyr Gly Asp Ala Leu Asp Tyr
1               5

<210> SEQ ID NO 20
<211> LENGTH: 9
<212> TYPE: PRT
<213> ORGANISM: Mus musculus

<400> SEQUENCE: 20

Trp Gln Gly Thr His Ser Pro Leu Thr
1               5

<210> SEQ ID NO 21
<211> LENGTH: 17
<212> TYPE: PRT
<213> ORGANISM: Mus musculus

<400> SEQUENCE: 21

Tyr Tyr Cys Gln His Ile Arg Glu Leu Thr Arg Ser Glu Gly Gly Pro
1               5                   10                  15

Ser

<210> SEQ ID NO 22
<211> LENGTH: 20
<212> TYPE: PRT
<213> ORGANISM: Mus musculus

<400> SEQUENCE: 22

Gly Val Tyr Tyr Cys Trp Gln Gly Thr His Ser Pro Leu Thr Phe Gly
1               5                   10                  15

Ala Gly Thr Lys
            20

<210> SEQ ID NO 23
<211> LENGTH: 20
<212> TYPE: PRT
<213> ORGANISM: Mus musculus
```

```
-continued

<400> SEQUENCE: 23

Gly Asp Ile Asn Pro Asn Asn Gly Tyr Thr Ile Tyr Asn Gln Lys Val
1               5                   10                  15

Lys Gly Lys Ala
            20

<210> SEQ ID NO 24
<211> LENGTH: 20
<212> TYPE: PRT
<213> ORGANISM: Mus musculus

<400> SEQUENCE: 24

Ala Val Tyr Tyr Cys Ala Arg Ser Gly Ser Arg Phe Asp Tyr Trp Gly
1               5                   10                  15

Glu Gly Thr Thr
            20

<210> SEQ ID NO 25
<211> LENGTH: 20
<212> TYPE: PRT
<213> ORGANISM: Mus musculus

<400> SEQUENCE: 25

Val Tyr Phe Cys Gln Gln Ser Asn Ser Trp Pro Val His Ala Arg Gly
1               5                   10                  15

Gly Gly Thr Lys
            20
```